US01209457982

(12) United States Patent
Jones

(10) Patent No.: US 12,094,579 B2
(45) Date of Patent: Sep. 17, 2024

(54) MACHINE-LEARNING METHOD AND APPARATUS TO ISOLATE CHEMICAL SIGNATURES

(71) Applicant: Oregon State University, Corvallis, OR (US)

(72) Inventor: Gerrad Jones, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 516 days.

(21) Appl. No.: 17/216,401

(22) Filed: Mar. 29, 2021

(65) Prior Publication Data

US 2021/0313016 A1 Oct. 7, 2021

Related U.S. Application Data

(60) Provisional application No. 63/005,090, filed on Apr. 3, 2020.

(51) Int. Cl.
*G16C 20/70* (2019.01)
*G01N 33/18* (2006.01)
*G01N 33/49* (2006.01)
*H01J 49/00* (2006.01)

(52) U.S. Cl.
CPC ............. *G16C 20/70* (2019.02); *G01N 33/18* (2013.01); *G01N 33/49* (2013.01); *H01J 49/0036* (2013.01)

(58) Field of Classification Search
CPC ..... G01N 33/18; G01N 33/49; H01J 49/0036; G06N 20/10; G16C 20/70
See application file for complete search history.

(56) References Cited

U.S. PATENT DOCUMENTS

| 6,898,533 | B1* | 5/2005 | Miller | G01N 21/25 702/30 |
| 2004/0121477 | A1* | 6/2004 | Thompson | G01N 33/6818 436/173 |
| 2008/0025591 | A1* | 1/2008 | Bhanot | G06F 18/40 382/224 |
| 2009/0098553 | A1* | 4/2009 | Guilford | G01N 33/57407 435/26 |
| 2009/0104602 | A1* | 4/2009 | Fernandez-Reyes | G01N 33/5695 435/6.15 |

(Continued)

OTHER PUBLICATIONS

Albergamo, V. et al., "Nontarget Screening Reveals Time Trends of Polar Micropollutants in a Riverbank Filtration", System. Environ. Sci. Technol. 2019, 53 (13), 7584-7594. https://doi.org/10.1021/acs.est.9b01750.

(Continued)

*Primary Examiner* — Michael J Dalbo
(74) *Attorney, Agent, or Firm* — MUGHAL GAUDRY & FRANKLIN PC

(57) ABSTRACT

A processing workflow centered on machine-learning algorithms that identifies a number of chemical features that can best distinguish the presence or absence of a chemical source. These chemical features are a chemical fingerprint that is unique to each source. The analysis workflow is rapid (e.g., fingerprints can be generated in minutes). The analysis workflow has wide-ranging applications such as detecting markers of pollution sources in rivers and fish tissues, forest pathogen outbreaks, and hard-to-diagnose diseases.

13 Claims, 5 Drawing Sheets

(56) References Cited

U.S. PATENT DOCUMENTS

| | | | | |
|---|---|---|---|---|
| 2013/0124108 | A1* | 5/2013 | Eiler | G16C 20/20 |
| | | | | 702/27 |
| 2019/0170712 | A1* | 6/2019 | Ueda | G01N 30/72 |
| 2020/0357520 | A1* | 11/2020 | Fujimoto | G16H 50/50 |
| 2021/0113673 | A1* | 4/2021 | Boucher | G16B 20/20 |

OTHER PUBLICATIONS

Carpenter, C. et al., "Fall Creek Monitoring Station: Highly Resolved Temporal Sampling to Prioritize the Identification of Nontarget Micropollutants in a Small Stream", Environ. Sci. Technol. 2019, 53 (1), 77-87. https://doi.org/10.1021/acs.est.8b05320.

Chiaia-Hernandez, A. et al., "Unravelling Contaminants in the Anthropocene Using Statistical Analysis of Liquid Chromatography-High-Resolution Mass Spectrometry Nontarget Screening Data Recorded in Lake Sediments", Environ. Sci. Technol. 2017, 51 (21), 12547-12556. https://doi.org/10.1021/acs.est.7b03357.

Cotton, J. et al., "Development and Validation of a Multiresidue Method for the Analysis of More than 500 Pesticides and Drugs in Water Based on On-Line and Liquid Chromatography Coupled to High Resolution Mass Spectrometry", Water Res. 2016, 104, 20-27. https://doi.org/10.1016/J.WATRES.2016.07.075.

Du, B. et al., "Development of Suspect and Non-Target Screening Methods for Detection of Organic Contaminants in Highway Runoff and Fish Tissue with High-Resolution Time-of-Flight Mass Spectrometry", Environ. Sci. Process. Impacts 2017, 19 (9), 1185-1196. https://doi.org/10.1039/C7EM00243B.

Hollender, J. et al., "Comprehensive Micropollutant Screening Using LC-HRMS/MS at Three Riverbank Filtration Sites to Assess Natural Attenuation and Potential Implications for Human Health", Water Res. X 2018, 1, 00007.

Hug, C. et al., "Linking Mutagenic Activity to Micropollutant Concentrations in Wastewater Samples by Partial Least Square Regression and Subsequent Identification of Variables", Chemosphere 2015, 138, 176-182. https://doi.org/10.1016/j.chemosphere.2015.05.072.

Kiss, A. et al., "Chemometric and High-Resolution Mass Spectrometry Tools for the Characterization and Comparison of Raw and Treated Wastewater Samples of a Pilot Plant on the SIPIBEL Site", Environ. Sci. Pollut. Res. 2018, 25 (10), 9230-9242. https://doi.org/10.1007/s11356-017-0748-x.

Masiá, A et al., "Ultra-High Performance Liquid Chromatography-Quadrupole Time-of-Flight Mass Spectrometry to Identify Contaminants in Water: An Insight on Environmental Forensics", J. Chromatogr. A 2014, 1345, 86-97. https://doi.org/10.1016/J.CHROMA.2014.04.017.

Peter, K. et al., "Using High-Resolution Mass Spectrometry to Identify Organic Contaminants Linked to Urban Stormwater Mortality Syndrome in Coho Salmon", Environ. Sci. Technol. 2018, 52 (18), 10317-10327. https://doi.org/10.1021/acs.est.8b03287.

Schollée, J. et al., "Non-Target Screening to Trace Ozonation Transformation Products in a Wastewater Treatment Train Including Different Post-Treatments", Water Res. 2018, 142, 267-278. https://doi.org/10.1016/J.WATRES.2018.05.045.

Schollée, J. et al., "Prioritizing Unknown Transformation Products from Biologically-Treated Wastewater Using High-Resolution Mass Spectrometry, Multivariate Statistics, and Metabolic Logic", Anal. Chem. 2015, 87 (24), 12121-12129. https://doi.org/10.1021/acs.analchem.5b02905.

Ziarrusta, H. et al., "Amitriptyline at an Environmentally Relevant Concentration Alters the Profile of Metabolites Beyond Monoamines in Gilt—Head Bream. Environ", Toxicol. Chem. 2019, 38 (5), 965-977. https://doi.org/10.1002/etc.4381.

* cited by examiner

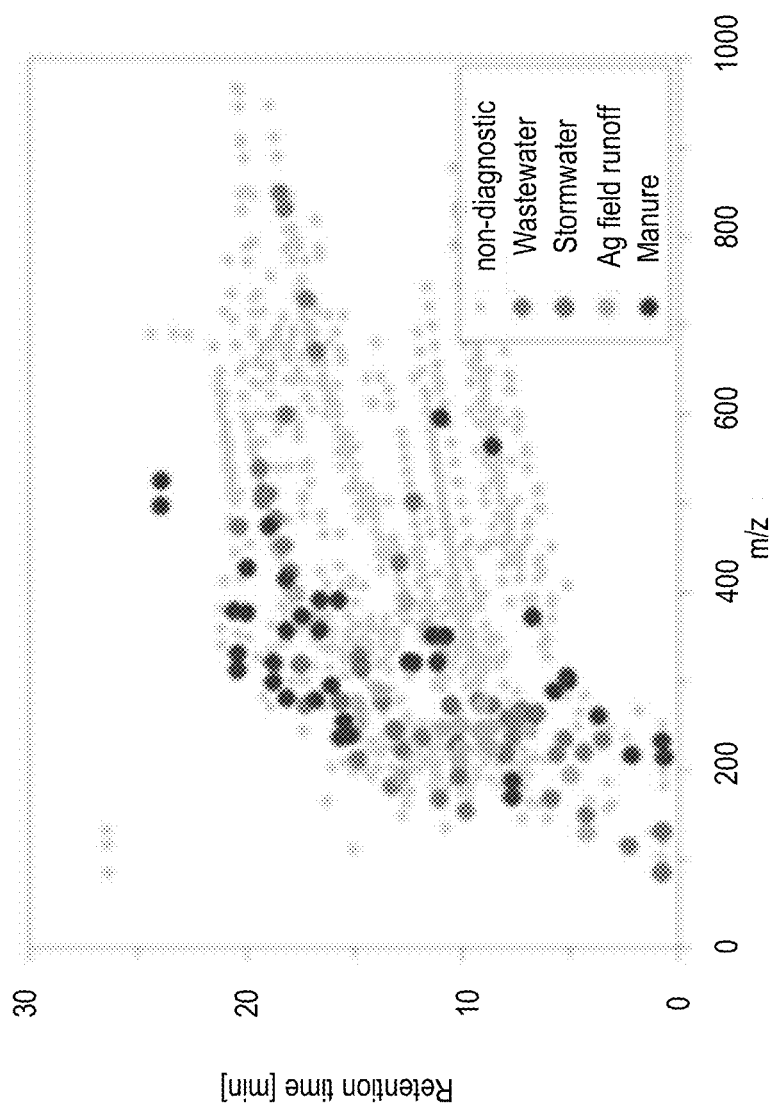

MACHINE-LEARNING METHOD AND APPARATUS TO ISOLATE CHEMICAL SIGNATURES

CLAIM FOR PRIORITY

This application claims the benefit of priority to U.S. Provisional Patent Application No. 63/005,090, filed on Apr. 3, 2020, and which is incorporated by reference in entirety.

BACKGROUND

Groundwater and surface water pollution present a substantial threat to human and ecosystem health. Consequently, policy makers, environmental agencies, and water managers often make efforts to monitor water quality and identify the chemical sources of pollutants whenever identification is practicable.

Some chemical pollutants, such as pharmaceuticals and other human made compounds (e.g., caffeine) typically have very specific sources. In theory, the presence of such compounds in drinking water could easily be used to indicate the pollution source contaminating the water supply. Other pollutants, such as nitrate and phosphorus, have multiple sources (e.g., fertilizer, animal wastes, septic tanks, road runoff, and others). Thus, the presence of such chemicals in water samples provides little indication of the possible (or most directly responsible) source. Identifying pollution sources becomes increasingly challenging further downstream as more water bodies converge and mix. As a result, water managers are unable to implement targeted strategies that are designed to eliminate pollution discharge.

In addition to specific pollutants or toxic compounds, tens of thousands of chemicals are present in the environment and originate from a wide variety of natural and manmade sources. Natural chemicals originate from the degradation of leaves and other organic material present within the environment, whereas manmade chemicals come from a variety of sources including runoff from streets, parking lots, agriculture fields, factories, and treatment facilities.

BRIEF DESCRIPTION OF THE DRAWINGS

The embodiments of the disclosure will be understood more fully from the detailed description given below and from the accompanying drawings of various embodiments of the disclosure, which, however, should not be taken to limit the disclosure to the specific embodiments, but are for explanation and understanding only.

FIGS. 2A-B illustrate an output from the chemical fingerprinting workflow.

DETAILED DESCRIPTION

Figure 1:
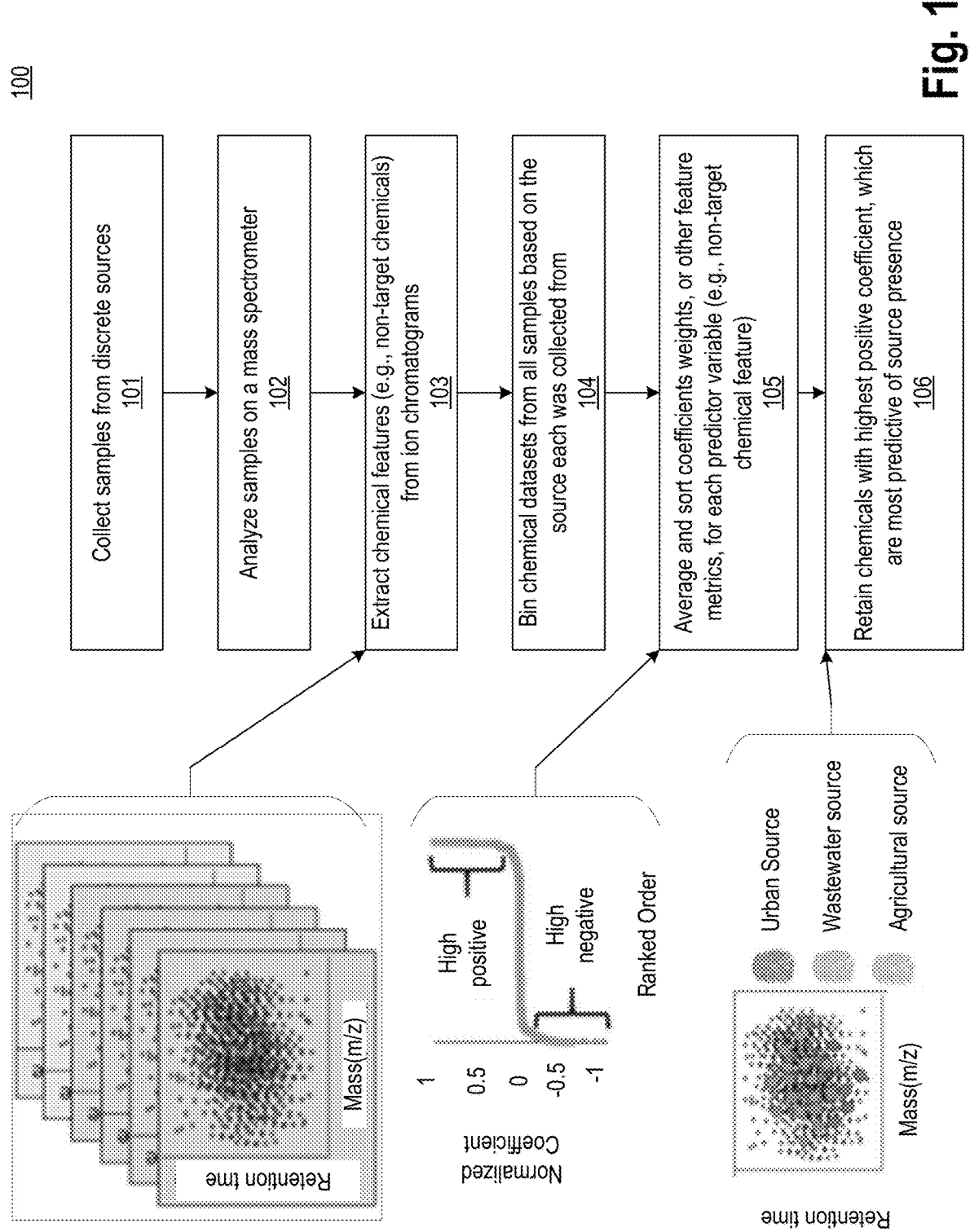
FIG. 1 illustrates a system architecture with major modules and components to isolate chemical signatures, in accordance with some embodiments.

Given the extreme diversity of chemicals in the environment, it is extremely unlikely that any two chemical sources share the exact same chemical composition or "fingerprint." Thus, it is expected that the chemical composition of different sources is unique.

Experts have previously theorized that it may be possible to distinguish different sources of pollutants simply by recognizing the chemical fingerprints associated with each source. While it might be challenging or impossible to identify a chemical source simply by testing for the presence of a specific pollutant in a mixed water sample (or a sample containing water from multiple sources), it is possible (in theory) to identify the source of a pollutant by testing for the unique chemical fingerprint of the source.

Chemical detection within the environment is currently accomplished using a variety of methods. Many chemicals can only be detected using mass spectrometry instruments (compared to a probe). For over 80 years, mass spectrometry instruments have been used to quantify chemicals within the environment. For most of this time, a process called targeted chemical analysis has been used to quantify the presence of different chemicals within the environment. Using a set of mass filters within a mass spectrometer, the vast majority of chemicals are removed during analysis. The chemicals that remain represent a small fraction of the entire pool. Targeted methods are useful because they help to remove noise that can make quantification difficult; however, they are merely useful when specific compounds are selected before instrument analysis is performed.

Recently, advances in mass spectrometry instruments have made it possible to quantify all chemicals that hit an instrument's detector. Instead of quantifying only target or known chemicals, these instruments can semi-quantitatively measure all chemical features that hit the detector of an instrument. This process is called non-target analysis. During non-target analysis, several thousand chemicals can be measured within a sample. Thus, non-target chemical datasets could be useful for developing chemical fingerprints of different sources because they contain thousands of quantifiable chemicals, some of which could be diagnostic of a source. Unlike targeted analyses where only known compounds are screened for, non-target analysis allows scientists to quantify unknown compounds as well.

Instead of testing a water sample for a specific chemical or pollutant, one could test for a chemical fingerprint (consisting of 10's of diagnostic chemicals) that is diagnostic of a pollution source. This is useful because there may not be any single chemical to test for that is indicative of a source, or when the pollutant of interest has multiple sources (e.g., nitrate). Although thousands of chemicals are present in a sample, it is likely that some chemicals are more useful as chemical fingerprints compared to others. It would be advantageous to measure only, for example, 10-100 of the most important chemicals. This theoretical subset of chemicals would thus represent a diagnostic chemical signature or fingerprint. This has been the subject of recent research, but identifying these diagnostic chemical signatures remains an unsolved problem.

The world's most advanced practitioners generally use the following types of approaches to address the problem: cluster analysis, co-occurrence, variable importance, and recognition.

Cluster analysis: Few suitable multivariate or data mining techniques have been used, with the most common being cluster analysis, both k-means and hierarchical. Clustering is a data mining approach that assigns group membership based on calculated chemical similarity. For non-target chemical data, samples with increasingly similar chemical composition will be grouped together. K-means and hierarchical clustering have assumptions that must be met (e.g., spherical clusters, similar sized clusters) to avoid gross misrepresentation of actual clusters; however, none of the above studies acknowledge or test these assumptions. Therefore, it is challenging to evaluate the validity of their results. Nevertheless, clustering merely provides information on chemical similarity and provides no information on chemical features driving group assignments, which is one goal of the various embodiments. Furthermore, cluster analysis assigns samples to a single category and provides no insight into how many pollution sources are present in mixed samples (e.g., creeks). Therefore, clustering is inappropriate for chemical fingerprinting.

Co-occurrence: Venn Diagrams are used to identify chemical features that co-occur both in tissue of deceased salmon following unexpected die off events and automotive fluids, the hypothesized mortality drivers. The assumption is that the co-occurring chemicals are the causative agents of die-off events; however, co-occurrence can be overly simplistic. First, Venn diagrams rely on presence or absence of data to find co-occurrences, which skews the results to chemical features that are widespread and abundant. Rare compounds, even if they are diagnostic, are likely to be excluded using Venn analysis. Second, all peak intensity information is lost when converted into a presence or absence format. Therefore, pollution sources with very similar chemical compositions (e.g., dairy versus beef versus swine manure) cannot be distinguished using co-occurrence. These sources are expected to have varying chemical ratios; therefore, intensity information should be included when identifying diagnostic chemical fingerprints. Thus, co-occurrence is inappropriate for chemical fingerprinting.

Variable importance: A few studies employ ordination techniques, almost exclusively principal components analysis (PCA) and partial least squares (PLS) regression/PLS discriminant analysis, to reveal patterns in non-target data. Briefly, PCA captures chemical gradients present within a dataset and summarizes those gradients into a reduced number of uncorrelated components. It is demonstrated that different sources (e.g., influent/effluent, wastewater/surface water) are strongly differentiated by the chemical gradients present in each sample. Because of this strong differentiation, PCA has been used to fingerprint sources. However, this may be a fundamental mischaracterization of PCA. Instead of identifying the specific chemical features that distinguish sources, PCA summarizes all the chemical variability present within a dataset. In essence, PCA, and other ordination techniques, is the exact opposite of chemical fingerprinting. PCA can identify the chemical gradients (not individual features) that distinguish groups, while it is possible to use factor loadings to interpret the important chemicals most related to each gradient, the correlation coefficients between the chemical features and the principal components are very weak (e.g., $|r|<0.05$) given the sheer number of chemical features, thus making objective fingerprinting with PCA challenging.

Similar to PCA, PLS has been used to capture chemical gradients that best predict other datasets, typically bioassays (e.g., toxicity, mutagenicity). Note that PLS has merely been used with continuous datasets within the non-target chemical literature, whereas source fingerprinting requires categorical data. PLS is advantageous over PCA because the importance of variables can be ranked. Thus, PLS classification could be used to develop a diagnostic fingerprint similar to what is described within; however, as it has been used in regression analysis, the number of important chemical features retained is high relative to the total number of chemical features (e.g., >200 predictive features from ~1500 total, or 14% of all data), which is undesirable for a predictive chemical signature. Thus, PLS has not been used successfully to develop a chemical fingerprint.

Recognition: Recognition algorithms can be used to recognize the presence of different patterns within a chemical dataset. These are commonly used for image analysis. These tools have not been applied to non-target chemical datasets, in part because their application would be highly impractical. Recognition algorithms require large training datasets (e.g., hundreds to thousands of samples per category). At a cost of $10-$100's per sample, it would be cost-prohibitive to collect enough representative samples to use recognition algorithms to identify the diagnostic chemical features associated with a particular process.

Various embodiments address the above need in a way that avoids the deficiencies that are described in the previous sections. Based on the thousands of chemical features within a given sample, some embodiments use a processing workflow centered on machine-learning algorithms that identifies, for example, the approximately 20-100 chemical features that can best distinguish the presence or absence of a chemical source. (Note: This choice of 20 to 100 features is completely arbitrary. Some fingerprinting exercises may use a greater number. For others, somewhat less). These chemical features can be thought of as a chemical fingerprint that is unique to each source.

The analysis workflow of various embodiments is rapid (e.g., fingerprints can be generated in minutes) and overcomes the limitations associated with the above described techniques. The analysis workflow of various embodiments has wide-ranging applications such as detecting markers of pollution sources in rivers, fish tissues, forest pathogen outbreaks, and hard-to-diagnose diseases.

The term "module" may refer to one or more software, hardware, passive and/or active components that are arranged to cooperate with one another to provide a desired function.

Throughout the specification, and in the claims, the term "connected" means a direct connection, such as electrical, mechanical, software, or magnetic connection between the things that are connected, without any intermediary devices or logic statements.

The term "coupled" means a direct or indirect connection, such as a direct electrical, mechanical, software or magnetic connection between the things that are connected or an indirect connection, through one or more passive or active intermediary devices.

The terms "substantially," "close," "approximately," "near," and "about," generally refer to being within +/−10% of a target value. For example, unless otherwise specified in the explicit context of their use, the terms "substantially equal," "about equal" and "approximately equal" mean that there is no more than incidental variation between among things so described. In the art, such variation is typically no more than +/−10% of a predetermined target value.

The term "adjacent" here generally refers to a position of a thing being next to (e.g., immediately next to or close to with one or more things between them) or adjoining another thing (e.g., abutting it).

Unless otherwise specified the use of the ordinal adjectives "first," "second," and "third," etc., to describe a common object, merely indicate that different instances of like objects are being referred to, and are not intended to imply that the objects so described must be in a given sequence, either temporally, spatially, in ranking or in any other manner.

For the purposes of the present disclosure, phrases "A and/or B" and "A or B" mean (A), (B), or (A and B). For the purposes of the present disclosure, the phrase "A, B, and/or C" means (A), (B), (C), (A and B), (A and C), (B and C), or (A, B and C).

The terms "left," "right," "front," "back," "top," "bottom," "over," "under," and the like in the description and in the claims, if any, are used for descriptive purposes and not necessarily for describing permanent relative positions.

FIG. 1 illustrates a system workflow architecture 100 with high-level modules and components to isolate chemical signatures, in accordance with some embodiments. Various blocks of the workflow architecture 100 are illustrated in a particular order. However, the order can be modified. For example, some blocks may be performed in parallel. The various blocks here can be performed by hardware, software, or a combination of them. In some embodiments, architecture 100 takes the form of a machine-learning workflow. As shown herein, this workflow has multiple operations that starts with several thousand chemical features and identifies the approximately, for example, 10 to 50 variables that have the best diagnostic capabilities.

The workflow begins at block 101 with collecting samples from discrete sources. These sources could be pollution (e.g., agricultural runoff, road runoff, effluent from a wastewater treatment plant) or other sources (e.g., blood samples from healthy and unhealthy individuals).

At block 102, samples are processed in a laboratory to prepare samples for non-target chemical analysis. There are various of sample preparation methods (e.g., solid phase extraction). Samples are injected into a high-resolution mass spectrometer (e.g., Time of Flight, Orbitrap mass spectrometer) to obtain a chemical feature dataset. In some embodiments, chemicals (e.g., non-polar organics) are extracted from the water samples and analyzed on a high-resolution mass spectrometer.

At block 103, non-target chemical features, or even a suitable number of target chemical features, are obtained from the mass spectrometer. Data is processed using standard manual approaches for processing targeted chemical data or software tools for processing non-targeted chemical data. In some examples, non-target chemical features that are uniquely identifiable based on their mass and retention time are obtained in full-scan mode (MS1) from all samples.

At block 104, the chemical datasets from all samples are binned using uniquely identifiable groups (e.g., the sources they were collected from). These bins are converted into dummy variables comprising of 1s and 0s for each source. 1s represent the samples from the source of interest and 0s indicate everything but the specific source (i.e., an outgroup). As such, each source is binned into individual categories and analyzed using support vector classification on comparable supervised classification algorithms. This type of multiclass classification is termed one-versus-all classification.

In some embodiments, a supervised classification algorithm is trained to minimize overfitting using standard cross validation techniques. Once overfitting is minimized and deemed suitable, the classification algorithm is trained to recognize the differences between the two groups (I/O) based on the chemical composition of all samples. In supervised classification sample pixels in an image or data set that are representative of specific classes are selected. A user specifies the various pixel values or spectral signatures that should be associated with each class. This is done by selecting representative sample sites of a known cover type called Training Sites or Areas. A computer algorithm then uses the spectral signatures from these training areas to classify the whole image or set of data. Examples of classification algorithms include maximum likelihood, minimum distance, Mahalanobis distance, and spectral angle mapper.

Many classification algorithms generate a coefficient that can be used to calculate the importance of each predictor variable (e.g., chemical features in this case) based on its ability to correctly discriminate groups. In this example, support vector classification is used, but other algorithms are appropriate, including neural network, random forest, gradient boosting, and others.

Instead of relying on a single iteration to calculate the importance, the importance value of each chemical feature is calculated and averaged over 1000 iterations as indicated by block 105. For each iteration, the training (e.g., 75% of the data) and testing (e.g., 25% of the data) datasets are randomized. Support vector classification is advantageous because chemical features with positive coefficients are associated with the presence of a particular group (1) and negative coefficients are associated with the absence of said group (0). Often, other classification algorithms generate only positive importance coefficients regardless if a chemical is predictive of source's presence or absence. Nevertheless, the importance coefficients can still be useful for predictive purposes. If negative and positive coefficients are necessary, this information can be found through other methods (e.g., sensitivity analysis). The workflow of various embodiments identifies the chemical signatures that are predictive of each source. In various embodiments, the process is iterated for each group to generate the chemical signatures for each source.

The importance coefficients for each group are averaged and sorted in block 105. The vast majority of chemicals have little to no predictive value and have a mean importance near 0. To facilitate comparison, all (or substantially all) coefficients are normalized based on the largest positive/negative coefficient such that the coefficients range from −1 to 1. In this manner, the chemical features with coefficients closer to 1 and −1 are increasingly important predictors of a chemical source's presence or absence, respectively.

Based on the sorted coefficients, the subset of chemical features that best predict a source (i.e., the chemical fingerprint) can be identified at block 106 using a variety of standard methods. For example, the mean coefficient score is approximately zero, whether negative or positive. Thus, coefficient averages that are statistically different from the mean (e.g., outliers) could be used to identify fingerprints.

Alternatively, to limit the number of chemical features for each fingerprint, an arbitrary number could be used (e.g., the 50 chemicals with the largest positive and negative importance coefficient values). Furthermore, the most important chemicals could be added stepwise into the classification models until the model performance peaks or plateaus. Any of these methods could be used to identify the boundary or threshold between important and non-important variables. Once a suitable threshold is reached, those chemicals together represent the chemical fingerprint.

Note that the method to determine when the critical threshold is reached is not as significant as creating a binary dummy variable comprising the source of interest and the outgroup. It is important to have a diverse outgroup. In the worst-case scenario, two pollution sources (A and B) are screened. In this scenario, the resulting chemical signatures will be those that best distinguish A from B, and those chemical signatures may not distinguish A from anything else. As the number of sources increases (e.g., as the outgroup becomes increasingly diverse), the resulting chemical signature becomes increasingly diagnostic.

Note that operations 104 through 106 are repeated for each source. For example, if 5 sources are present, 5 different fingerprints are generated with bin 1 corresponding to the source, and bin 0 corresponding to everything else. The positive and negative importance coefficients correspond to the chemical features that are most predictive of the source presence (1) and absence (0), respectively. Unlike previous techniques, which fail to identify boundaries between important and non-important variables, the technique of various embodiments better identifies the most important diagnostic chemicals.

In preliminary data, the workflow architecture 100 of FIG. 1 is able to find 10-50 diagnostic chemical features for each source. Once the subset of diagnostic features are found, it is possible to screen a single sample for these features; thus, it is possible to screen a single sample for the presence/absence of any number of fingerprinted sources. The architecture of various embodiments recognizes that chemical fingerprinting is not merely supervised classification. One goal of supervised classification is to categorize a sample into the single group that best matches the composition of the entire dataset. If multiple sources are present in a mixed sample, supervised classification is unable to identify the presence of multiple sources. For example, if a sample is composed of 90% A and 10% B, traditional classification will fail to recognize the presence of B. Conversely, the goal of the chemical fingerprinting protocol described within is to predict whether or not one or more fingerprinted sources are contributing to the chemical composition of a sample based on the intensity of the diagnostic chemical signatures within that sample. The approach of various embodiments identifies the chemical features that best predict the presence/absence of each individual source. By identifying a subset of the input data that are diagnostic of each source, it is possible to test a mixed sample for any number of individual sources. The following example outlines the process of isolating chemical signatures relative to known methods.

Assume there are four pollution sources: A, B, C, and D. One could collect a variety of samples from each source, quantify the chemical composition of each, and use a classification algorithm that can simultaneously distinguish each source. There would be a suite of important chemicals that could be used as a chemical fingerprint that could distinguish only these sources, but there is a problem here. Based on the chemical composition, a classification algorithm would predict a sample to belong to one (and only one) of the four sources or bins (i.e., A, B, C, or D). Thus, the "important" chemical signature is dependent on the bins that are originally present.

If the samples contained 90% A and 10% B, the classification algorithm would place the sample into bin A because it is most similar to A. Traditional classification would thus overlook the presence of B in this situation. Using merely classification, the approach to recognize 90% A:10% B as its own source would be to add a new source bin. Instead of A, B, C, and D, one would have to add A+B. Thus, to test for combinations, one would need to manually mix samples and add those to the source list. For 4 sources (A, B, C, and D), the following mixtures are required: A+B, A+C, A+D, B+C, B+D, C+D, A+B+C, A+B+D, A+C+D, B+C+D, A+B+C+D.

Using merely classification, the combinations of sources matter because the chemical signature is dependent on the bins. This becomes increasingly complicated as the number of bins increases, and it becomes an insurmountable problem when considering the relative proportion of the mixtures. For example, a 90%: 10% mixture of A and B would be different from a 90%: 10 mixture of B and A. Considering all the combinations of chemicals and their relative proportions, the number of bins one would need to make becomes limiting, if not infinite. Thus, it would be useful to generate chemical fingerprints of pollution sources that are independent of proportions or combinations, which is what the technique of various embodiments does.

With the procedure of various embodiments, one can identify the chemical signatures that distinguish each source from everything else. Instead of considering A, B, C, and D together (as in the original example), the scheme of various embodiments is a binary analysis that identifies the chemical features that best distinguishes A from everything else (i.e., the bin B+C+D), the chemical features that best distinguishes B from everything else (i.e., the bin A+C+D), etc. In this manner, one could test for any combination simply by testing for the presence/absence of the original sources/bins without the need to make mixtures. The approach of various embodiments uses classification tools to first identify the diagnostic chemical signatures of a specific source in a binary system. Once the relevant source-specific fingerprints are identified through an iterative analysis, these specific fingerprints can be screened for in a sample to predict the presence/absence of a source.

Figure 2A:
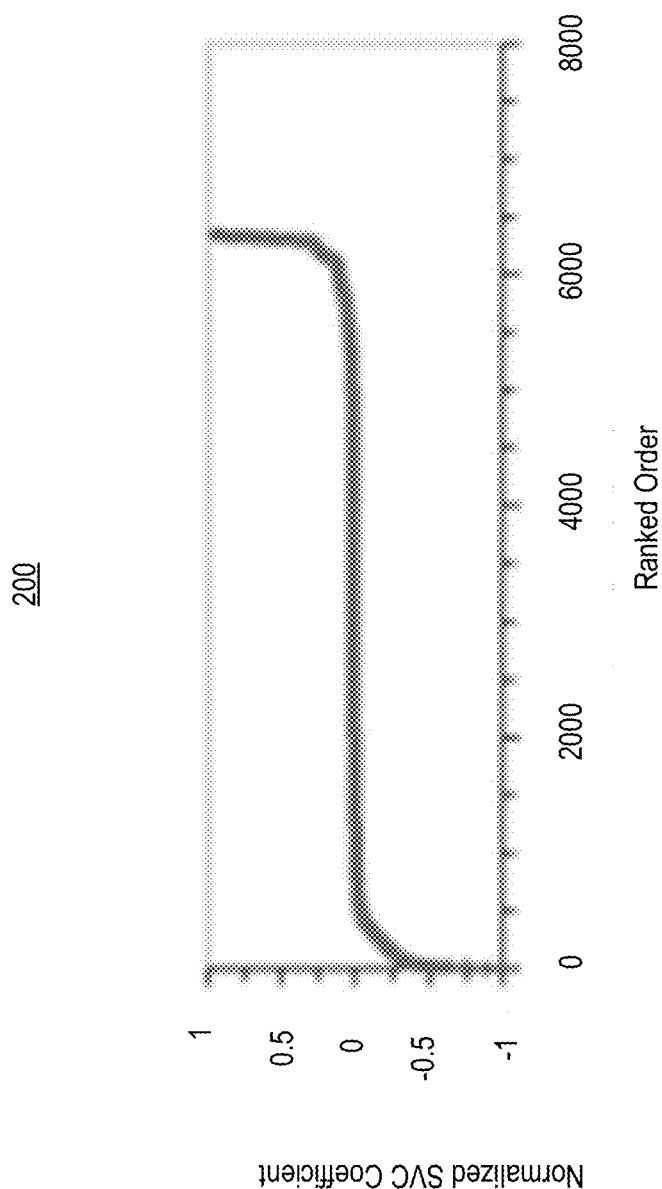

FIGS. 2A-B illustrate an output from the chemical fingerprinting workflow. FIG. 2A illustrates plot 200 that shows that there is a limited number of diagnostic features in environmental samples. Chemicals with an SVC coefficient close to 0 are not useful for diagnostics, and everything that is close to 1 or −1 is most important. FIG. 2B illustrates scatter plot 220 showing that samples from different sources have different fingerprints based on the pattern of diagnostic elements.

While the embodiments herein are described with reference to identifying chemical signatures that are diagnostic of different pollution sources and how to identify the presence of a particular source in a mixed water sample, the embodiments are not limited to such.

The workflow of some embodiments can also be used to address other types of needs and applications. For example, all biological, chemical, and physical processes in the environment generate a chemical signature that is uniquely distinguishable, and those chemical signatures can be identified for the presence of a particular source.

The workflow of some embodiments can be used for disease diagnoses. Some diseases are difficult to detect (e.g., colorectal cancer) or are only detectable after death (e.g., traumatic brain encephalopathy). Such diseases change the chemistry of the body in distinct ways. Using this workflow, it is possible to develop the chemical fingerprints that are best able to predict a healthy individual from an unhealthy individual. For example, simply by screening a blood, urine, fecal sample, etc., it is possible to screen an individual for innumerable chemical signatures.

The workflow of some embodiments can be used for ecosystem monitoring. Ecosystem monitoring is expensive and time consuming. For example, some forest pests, such as bark beetle, are monitored using aerial surveys conducted in planes, and detection only occurs after trees begin to die. The chemical signatures associated with healthy and unhealthy ecosystems is distinct. Simply by screening a water sample from the terminus of a watershed, it is possible to quantify ecosystem health within an entire watershed based on the chemical signatures present.

The workflow of some embodiments can be used for law enforcement. Illegal drug production occurs in houses (e.g., methamphetamines) and watersheds (e.g., marijuana). These activities are certain to produce unique chemical signatures.

By collecting sewer samples in neighborhoods or water samples in watersheds, law enforcement officials can detect illegal drug activities in our communities.

The workflow of some embodiments can exist as a standalone Python application. Once mass spectrometry data are fully processed, this software can be used by a user or machine to identify the diagnostic chemical signatures associated with a particular chemical source.

The workflow of some embodiments can exist as a web interface. Once mass spectrometry data are fully processed, a user or machine can upload a dataset for online analysis. This interface would be fully functional with little input from the user.

Figure 3:
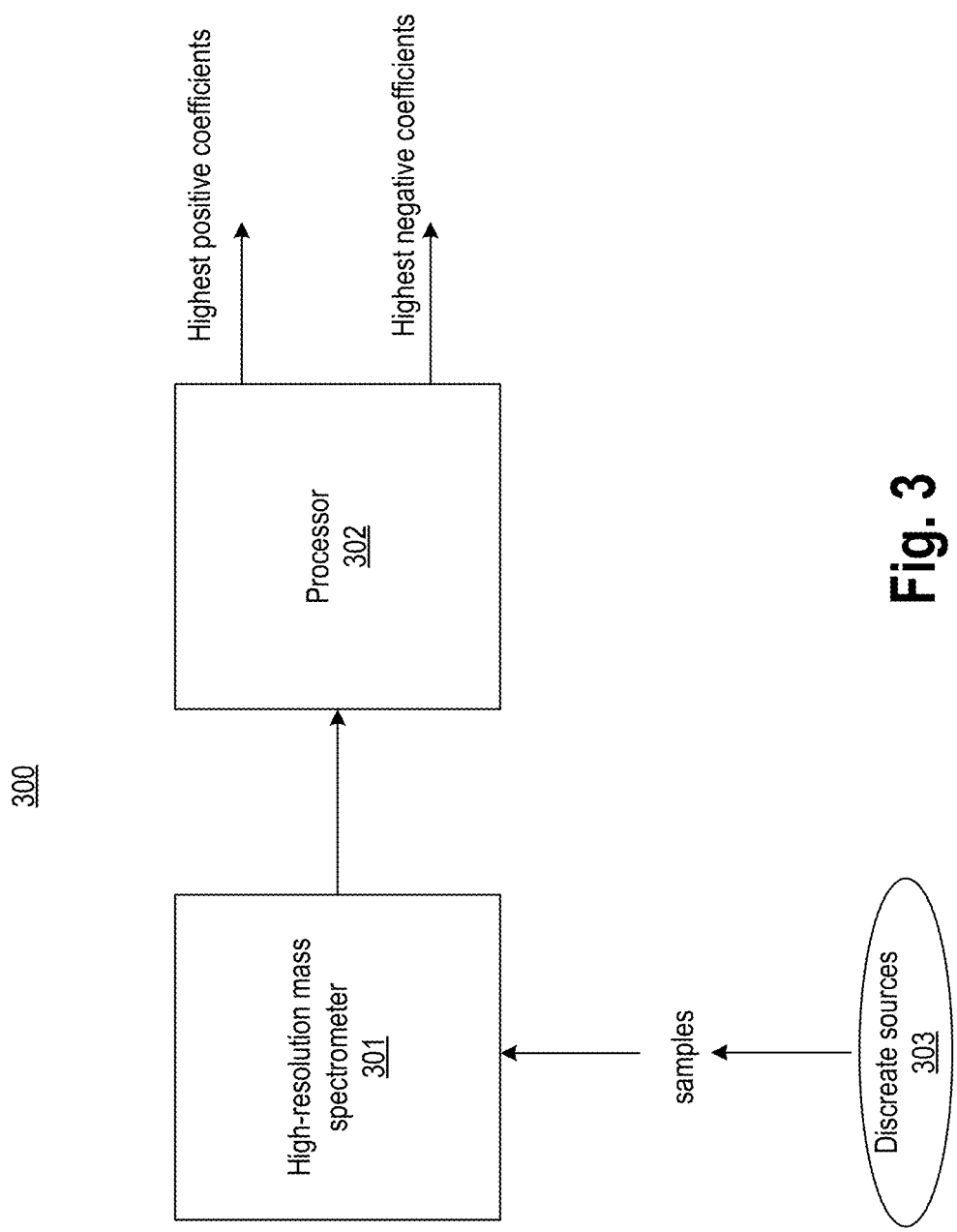
FIG. 3 illustrates an apparatus to isolate chemical signatures, in accordance with some embodiments.

FIG. 3 illustrates apparatus 300 to isolate chemical signatures, in accordance with some embodiments. The process performed by apparatus 300 uses classification tools to first identify the diagnostic chemical signatures of a specific source in a binary system. Once the relevant source-specific fingerprints are identified through an iterative analysis, these specific fingerprints can be screened for in a sample.

Apparatus 300 comprises a high-resolution mass spectrometer 301 and processor or computing device 302. Samples from discrete sources 303 are received by spectrometer 301 for analysis. Examples of discrete sources include one or more of: agricultural runoff, effluent from wastewater treatment plant, or blood samples from individuals. In some embodiments, high-resolution mass spectrometer 301 analyzes a binned source using a supervised classification process. Each source of a plurality of sources is binned into individual categories.

Processor or computing device 302 (e.g., a cloud server, local terminal, laptop, etc.) is communicatively coupled to high-resolution mass spectrometer 301 via wired or wireless means. In some embodiments, processor or computing device 302 averages and sorts coefficients for each predictor variable associated for each source. Based on the sorted coefficients, the subset of chemical features that best predict a source (i.e., the chemical fingerprint) can be identified.

In some embodiments, processor or computing device 302 selects chemicals with highest negative and positive coefficients from the sorted coefficients for each source. The positive and negative importance coefficients correspond to the chemical features that are most predictive of the source presence (1) and absence (0), respectively. The various operations performed by processor or computing device 302 are achieved by executing a software program that is used to isolate chemical signatures. The software program may be stored in a machine-readable media as discussed with reference to FIG. 4.

In various embodiments, non-target features associated with each source has associated non-target features which are based on mass and retention time that are obtained from substantially all samples. The non-target features are obtained via any suitable sample processing, such as solid phase extraction or direct injection, followed by instrument analysis. In some embodiments, processor or computing device 302 converts each binned source into variables comprising 1s and 0s for each source. Here, 1s represent samples from the source of interest and 0s indicate everything but a specific source. The process executed by processor or computing device 302 is performed iteratively. For example, the process of binning each source of a plurality of sources into individual categories, analyzing the binned source using a supervised classification process, averaging and sorting coefficients for each predictor variable associated for each source, in response to the analyzing; selecting chemicals with highest negative and positive coefficients from the sorted coefficients for each source, and converting each binned source into variables comprising 1s and 0s for each source is performed iteratively.

Figure 4:
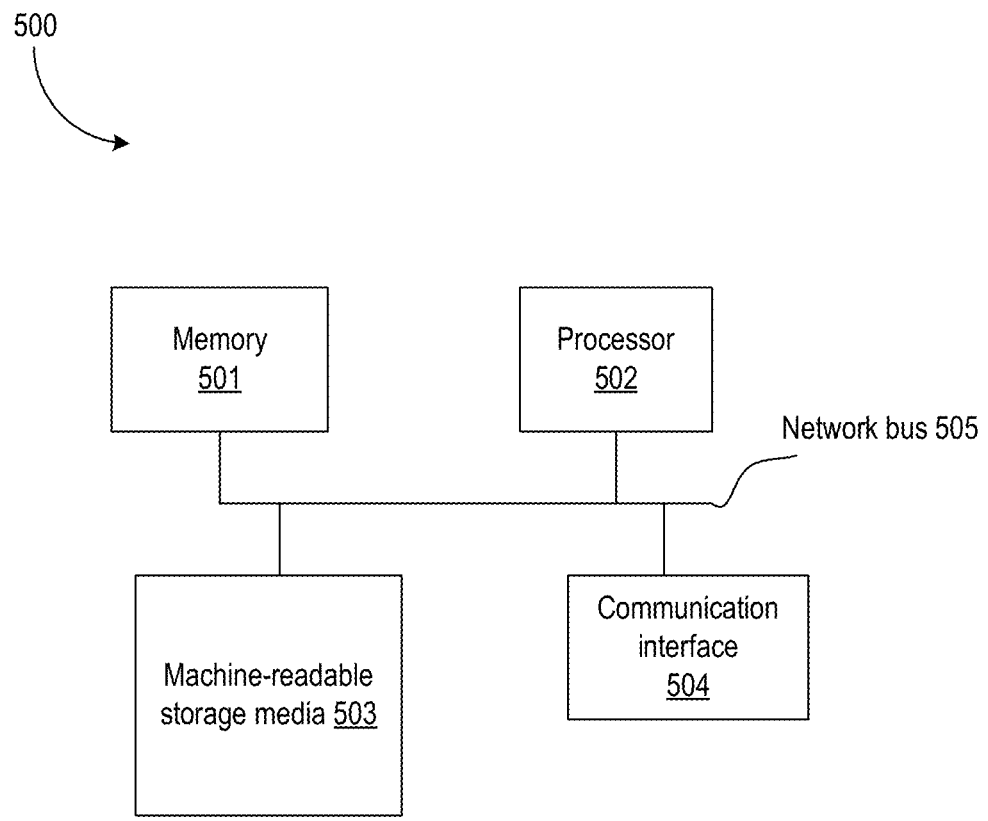
FIG. 4 illustrates a computer system which performs the workflow of FIG. 1, in accordance with some embodiments.

FIG. 4 illustrates computer system 500 which performs the workflow of FIG. 1, in accordance with some embodiments. Elements of embodiments (e.g., flowchart and scheme described with reference to FIG. 1) are also provided as a machine-readable medium (e.g., memory) for storing the computer-executable instructions (e.g., instructions to implement any other processes discussed herein). In some embodiments, computing platform 500 comprises memory 501, processor 502, machine-readable storage media 503 (also referred to as tangible machine-readable medium), communication interface 504 (e.g., wireless or wired interface), and network bus 505 coupled together as shown.

In some embodiments, processor 502 is a Digital Signal Processor (DSP), an Application Specific Integrated Circuit (ASIC), a general-purpose Central Processing Unit (CPU), or a low power logic implementing a simple finite state machine to perform the method of the flowchart and/or various embodiments, etc.

In some embodiments, the various logic blocks of system 500 are coupled together via network bus 505. Any suitable protocol may be used to implement network bus 505. In some embodiments, machine-readable storage medium 503 includes instructions (also referred to as the program software code/instructions) for calculating or measuring distance and relative orientation of a device with reference to another device as described with reference to various embodiments and flowchart.

Program software code/instructions associated with the flowcharts (and/or various embodiments) and executed to implement embodiments of the disclosed subject matter may be implemented as part of an operating system or a specific application, component, program, object, module, routine, or other sequence of instructions or organization of sequences of instructions referred to as "program software code/instructions," "operating system program software code/instructions," "application program software code/instructions," or simply "software" or firmware embedded in processor. In some embodiments, the program software code/instructions associated with flowcharts 200-400 (and/or various embodiments) are executed by system 500.

In some embodiments, the program software code/instructions associated with the flowchart (and/or various embodiments) are stored in a computer executable storage medium 503 and executed by processor 502. Here, computer executable storage medium 503 is a tangible machine-readable medium that can be used to store program software code/instructions and data that, when executed by a computing device, causes one or more processors (e.g., processor 502) to perform a method(s) as may be recited in one or more accompanying claims directed to the disclosed subject matter.

The tangible machine-readable medium 503 may include storage of the executable software program code/instructions and data in various tangible locations, including for example ROM, volatile RAM, non-volatile memory and/or cache and/or other tangible memory as referenced in the present application. Portions of this program software code/instructions and/or data may be stored in any one of these storage and memory devices. Further, the program software code/instructions can be obtained from other storage, including, e.g., through centralized servers or peer to peer networks and the like, including the Internet. Different portions of the software program code/instructions and data can be obtained at different times and in different communication sessions or in the same communication session.

In some embodiments, a machine-readable storage media is provided having machine-readable instructions stored thereon, that when executed, cause one or more machines to perform a method. The method comprises binning each source of a plurality of sources into individual categories; analyzing the binned source using supervised classification process; averaging and sorting coefficients for each predictor variable associated for each source, in response to the analyzing; and selecting chemicals with highest negative and positive coefficients from the sorted coefficients for each source. In some embodiments, each source is analyzed on a high-resolution mass spectrometer. In some embodiments, the non-target features associated with the source are based on mass and retention time and are obtained from substantially all samples.

In some embodiments, the non-target features are obtained via solid phase extraction or direct injection (or other suitable processing step). In some embodiments, the plurality of samples is collected from discrete sources. In some embodiments, the sources include one or more of: agricultural runoff, effluent from wastewater treatment plant, or blood samples from individuals. In some embodiments, method further comprises converting each binned source into variables comprising ones and zeros for each source, wherein ones represent samples from the source of interest and zeros indicate everything but a specific source. In some embodiments, the method of binning, analyzing, averaging and sorting, and identifying is performed iteratively.

The software program code/instructions (associated with the flowchart and other embodiments) and data can be obtained in their entirety, prior to the execution of a respective software program or application by the computing device. Alternatively, portions of the software program code/instructions and data can be obtained dynamically, e.g., just in time, when needed for execution. Alternatively, some combination of these ways of obtaining the software program code/instructions and data may occur, e.g., for different applications, components, programs, objects, modules, routines or other sequences of instructions or organization of sequences of instructions, by way of example. Thus, it is not required that the data and instructions be on a tangible machine-readable medium in entirety at a particular instance of time.

Examples of tangible computer-readable media 503 include but are not limited to recordable and non-recordable type media such as volatile and non-volatile memory devices, read only memory (ROM), random access memory (RAM), flash memory devices, floppy and other removable disks, magnetic storage media, optical storage media (e.g., Compact Disk Read-Only Memory (CD ROMS), Digital Versatile Disks (DVDs), etc.), among others. The software program code/instructions may be temporarily stored in digital tangible communication links while implementing electrical, optical, acoustical or other forms of propagating signals, such as carrier waves, infrared signals, digital signals, etc. through such tangible communication links.

In general, tangible machine-readable medium 503 includes any tangible mechanism that provides (i.e., stores and/or transmits in digital form, e.g., data packets) information in a form accessible by a machine (i.e., a computing device), which may be included, e.g., in a communication device, a computing device, a network device, a personal digital assistant, a manufacturing tool, a mobile communication device, whether or not able to download and run applications and subsidized applications from the communication network, such as the Internet, e.g., an iPhone®, Galaxy®, Blackberry® Nexus®, or the like, or any other device including a computing device. In one embodiment, processor-based system is in a form of or included within a PDA (personal digital assistant), a cellular phone, a notebook computer, a tablet, a game console, a set top box, an embedded system, a TV (television), a personal desktop computer, etc. Alternatively, the traditional communication applications and subsidized application(s) may be used in some embodiments of the disclosed subject matter.

While the disclosure has been described in conjunction with specific embodiments thereof, many alternatives, modifications and variations of such embodiments will be apparent to those of ordinary skill in the art in light of the foregoing description. The embodiments of the disclosure are intended to embrace all such alternatives, modifications, and variations as to fall within the broad scope of the appended claims.

Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments. If the specification states a component, feature, structure, or characteristic "may," "might," or "could" be included, that particular component, feature, structure, or characteristic is not required to be included. If the specification or claim refers to "a" or "an" element, that does not mean there is only one of the elements. If the specification or claims refer to "an additional" element, that does not preclude there being more than one of the additional elements.

Furthermore, the particular features, structures, functions, or characteristics may be combined in any suitable manner in one or more embodiments. For example, a first embodiment may be combined with a second embodiment anywhere the particular features, structures, functions, or characteristics associated with the two embodiments are not mutually exclusive.

While the disclosure has been described in conjunction with specific embodiments thereof, many alternatives, modifications and variations of such embodiments will be apparent to those of ordinary skill in the art in light of the foregoing description. The embodiments of the disclosure are intended to embrace all such alternatives, modifications, and variations as to fall within the broad scope of the appended claims.

Various embodiments are described as examples. The examples can be combined in any suitable manner. For instance, example 5 can be combined with example 3 and/or example 7.

Example 1: A machine-readable storage media having machine-readable instructions stored thereon, that when executed, cause one or more machines to perform a method comprising: binning each source of a plurality of sources into individual categories; analyzing the binned source using a supervised classification process; averaging and sorting coefficients for each predictor variable associated for each source, in response to the analyzing; and selecting chemicals with highest negative and positive coefficients from the sorted coefficients for each source.

Example 2: The machine-readable storage media of example 1, wherein each source is analyzed on a high-resolution mass spectrometer.

Example 3: The machine-readable storage media of example 1, wherein each source has associated non-target features that are based on mass and retention time that are obtained from substantially all samples.

Example 4: The machine-readable storage media of example 3, wherein the non-target features are obtained via instrument analysis following solid phase extraction or direct injection.

Example 5: The machine-readable storage media of example 1, wherein the plurality of sources is collected from discrete sources.

Example 6: The machine-readable storage media of example 5, wherein the discrete sources includes one or more of: agricultural runoff, effluent from wastewater treatment plant, or blood samples from individuals.

Example 7: The machine-readable storage media of example 1 having machine-readable instructions stored thereon, that when executed, cause the one or more machines to perform the method comprising: converting each binned source into variables comprising 1s and 0s for each source, wherein 1s represent samples from the source of interest and 0s indicate everything but a specific source.

Example 8: The machine-readable storage media of example 1, wherein the method of binning, analyzing, averaging and sorting, and selecting is performed iteratively.

Example 9: An apparatus comprising: a high-resolution mass spectrometer to analyze a binned source using a supervised classification process, wherein each source of a plurality of sources is binned into individual categories; and a processor communicatively coupled to the high-resolution mass spectrometer, wherein the processor is to: average and sort coefficients for each predictor variable associated for each source; and select chemicals with highest negative and positive coefficients from the sorted coefficients for each source.

Example 10: The apparatus of example 9, wherein non-target features associated with each source has associated non-target features which are based on mass and retention time that are obtained from substantially all samples.

Example 11: The apparatus of example 10, wherein the non-target features are obtained via instrument analysis following solid phase extraction or direct injection.

Example 12: The apparatus of example 9, wherein the plurality of sources is collected from discrete sources.

Example 13: The apparatus of example 12, wherein the discrete sources includes one or more of: agricultural runoff, effluent from wastewater treatment plant, or blood samples from individuals.

Example 14: The apparatus of example 9, wherein the processor is to convert each binned source into variables comprising 1s and 0s for each source, wherein 1s represent samples from the source of interest and 0s indicate everything but a specific source.

Example 15: The apparatus of example 9, wherein the processor is to iteratively bin, analyze, average, sort, and select.

Example 16: A method comprising: binning each source of a plurality of sources into individual categories; analyzing the binned source using supervised classification process; averaging and sorting coefficients for each predictor variable associated for each source; selecting chemicals with highest negative and positive coefficients from the sorted coefficients for each source; and converting each binned source into variables comprising 1s and 0s for each source, wherein 1s represent samples from the source of interest and 0s indicate everything but a specific source. Example 17: The method of example 16, wherein each source is analyzed on a high-resolution mass spectrometer.

Example 18: The method of example 16, wherein each source has associated non-target features that are based on mass and retention time that are obtained from substantially all samples, wherein the non-target features are obtained via instrument analysis following solid phase extraction or direct injection.

Example 19: The method of example 16, wherein the plurality of samples is collected from discrete sources.

Example 20: The method of example 19, wherein the discrete sources include one or more of: agricultural runoff, effluent from wastewater treatment plant, or blood samples from individuals.

An abstract is provided that will allow the reader to ascertain the nature and gist of the technical disclosure. The abstract is submitted with the understanding that it will not be used to limit the scope or meaning of the claims. The following claims are hereby incorporated into the detailed description, with each claim standing on its own as a separate embodiment.

What is claimed is:

1. A method for distinguishing a presence or absence of an individual chemical source of at least two chemical sources, the method comprising:
   receiving a plurality of samples from the at least two chemical sources, wherein an individual sample of the plurality of samples is associated with one or more predictor variables representing a chemical characteristic associated with a chemical source, from the at least two chemical sources, from which the individual sample was taken;
   analyzing the plurality of samples with a mass spectrometer to obtain a plurality of mass spectral data sets for each chemical source of the at least two chemical sources;
   storing the plurality of mass spectral data sets on a machine-readable storage medium;
   reading the plurality of mass spectral data sets by one or more processors; and
   executing a set of machine-readable instructions by the one or more processors to perform:
   binning a mass spectral data set for each individual chemical source of the at least two chemical sources into an individual bin to generate a binned source, wherein the binned source corresponds to an individual category of the at least two chemical sources;
   converting the individual bin into a binary variable comprising 1s and Os for the individual chemical source, wherein 1s represent one or more samples from a chemical source of interest and Os represent other chemical sources from the at least two chemical sources;
   selecting, based on a specification of a spectral signature derived from the mass spectral data set associated with the individual category, one or more representative sample sites;
   analyzing the binned source by applying a supervised classification process in which a machine-learning classifier is trained on the one or more representative sample sites to differentiate between first one or more samples of the chemical source of interest and second one or more samples of the other chemical sources from the at least two chemical sources based on an associated chemical composition;
   generating a set of coefficients for an individual predictor variable that evaluates a relevance of the individual predictor variable based on an ability to discriminate the spectral signature of the first one or more samples from the second one or more samples by applying the spectral signature of the one or more representative sample sites;

averaging and sorting coefficients of the set of coefficients for the individual predictor variable associated for the individual chemical source;

selecting chemicals with highest negative and positive coefficients from the sorted coefficients for the individual chemical source; and generating an output, based on the sorted coefficients for the individual chemical source, indicative of a subset of chemical features that predicts the individual chemical source.

2. The method of claim 1, wherein the mass spectrometer is a high-resolution mass spectrometer which obtains an individual mass spectral data set, and wherein the individual mass spectral data set comprise mass and retention time data.

3. The method of claim 1, wherein the individual chemical source has one or more associated non-target, target, and/or suspect features that are based on mass and retention time data that are obtained from the mass spectral data set of substantially all samples taken from the individual chemical source.

4. The method of claim 3, wherein the one or more associated non-target, target, and/or suspect features are obtained via instrument analysis following chemical extraction or direct injection.

5. The method of claim 1, wherein the individual chemical sources of the at least two chemical sources is a discrete chemical source.

6. The method of claim 5, wherein the discrete chemical source included one or more of: agricultural runoff, effluent from wastewater treatment plant, or blood samples from individuals.

7. The method of claim 1, wherein the method of binning, analyzing, averaging and sorting, and selecting is performed iteratively.

8. An apparatus comprising:
a high-resolution mass spectrometer to analyze a plurality of samples from at least two chemical sources; and
one or more processors processor communicatively coupled to the high-resolution mass spectrometer, wherein the one or more processors is to:
bin an individual chemical source of the at least two chemical sources into an individual bin to generate a binned source, wherein the binned source corresponds to an individual category of the at least two chemical sources;
convert the individual bin into a binary variable comprising 1s and 0s for the individual chemical source, wherein 1s represent one or more samples from a chemical source of interest and 0s represent other chemical sources from the at least two chemical sources;
select, based on a specification of a spectral signature associated with the individual category, one or more representative sample sites;
analyze, for the individual chemical source, the binned source by application of a supervised classification process in which a machine-learning classifier is trained on the one or more representative sample sites to differentiate between first one or more samples of the chemical source of interest and second one or more samples of the other chemical sources from the at least two chemical sources based on an associated chemical composition;
generate coefficients for an individual predictor variable that evaluates a relevance of the individual predictor variable based on an ability to discriminate the spectral signature of the first one or more samples from the second one or more samples by application of the spectral signature of the one or more representative sample sites;
average and sort the coefficients for the individual predictor variable associated for the individual chemical source;
select chemicals with highest negative and positive coefficients from the coefficients for the individual chemical source; and
generate an output, based on the coefficients for the individual chemical source, indicative of a subset of chemical features that predicts the individual chemical source.

9. The apparatus of claim 8, wherein the individual chemical source has associated non-target features which are based on mass and retention time that are obtained from substantially all samples.

10. The apparatus of claim 9, wherein the associated non-target features are obtained via instrument analysis following solid phase extraction or direct injection.

11. The apparatus of claim 8, wherein the plurality of samples is collected from discrete chemical sources.

12. The apparatus of claim 11, wherein the discrete chemical sources include one or more of: agricultural runoff, effluent from wastewater treatment plant, or blood samples from individuals.

13. The apparatus of claim 8, wherein the one or more processors is to iteratively average, sort, and select.

* * * * *